United States Patent [19]

Shipchandler

[11] 4,046,817
[45] Sept. 6, 1977

[54] METHOD OF SYNTHESIS OF PYROGALLOL

[75] Inventor: Mohammed T. Shipchandler, Terre Haute, Ind.

[73] Assignee: IMC Chemical Group, Inc., Maryland

[21] Appl. No.: 658,422

[22] Filed: Feb. 17, 1976

Related U.S. Application Data

[63] Continuation-in-part of Ser. No. 490,156, July 19, 1974, abandoned.

[51] Int. Cl.$^2$ .................. C07C 39/10; C07C 69/38; C07C 69/66
[52] U.S. Cl. ................ 260/621 R; 260/625; 260/521 P; 560/126; 560/180
[58] Field of Search ............ 490/156; 260/468 K, 260/621 R, 625, 521 R, 484 R

[56] References Cited

U.S. PATENT DOCUMENTS

| 2,782,220 | 2/1957 | Ingram | 260/468 K |
| 2,782,221 | 2/1957 | Reed | 260/468 K |
| 2,782,223 | 2/1957 | Reed | 260/468 K |
| 2,803,644 | 8/1957 | Lenel | 260/468 K |

OTHER PUBLICATIONS

Rinderknecht, "J. Amer. Chem. Soc.," vol. 10 (1948) pp. 2605-2606.

*Primary Examiner*—James O. Thomas, Jr.
*Assistant Examiner*—W. B. Lone

[57] ABSTRACT

A process for the synthesis of pyrogallol from glutaric ester and dialkoxymalonic ester.

5 Claims, No Drawings

METHOD OF SYNTHESIS OF PYROGALLOL

CROSS-REFERENCE TO RELATED APPLICATION

This application is a continuation-in-part of applicant's copending application Ser. No. 490,156, filed July 19, 1974, now abandoned.

BACKGROUND OF THE INVENTION

This invention relates to a process for the preparation of pyrogallol. In a particular aspect, it relates to a process for the preparation of pyrogallol from glutaric ester and dialkoxymalonic ester.

Pyrogallol has many important uses, e.g. in photographic developers, as a mordant for wool, and in staining of leather. It is usually prepared from gallic acid by heating as described by Rinderknecht and Niemann, J. Am. Chem. Soc. 70, 2605 (1948), although Stevens in U.S. Pat. No. 2,603,662 disclosed a process involving chlorination of p-tert. butylphenol and hydroysis of the product. Gallic acid is made principally by saponification of natural product tannic acids which are chiefly obtained from nutgalls gathered in Turkey and from Tara powder obtained from a plant species found at high altitudes in the Peruvian Andes. A method of synthesis has been disclosed by C. D. Hurd, U.S. Pat. No. 3,560,569. Nevertheless, gallic acid and pyrogallol are high-priced commodities which undoubtedly have been kept from many markets where they would be widely used at a lower price.

SUMMARY OF THE INVENTION

It is an object of this invention to provide a new process for the preparation of pyrogallol.

A second object of this invention is to provide a process for the preparation of pyrogallol from glutaric ester and dialkoxymalonic ester.

Another object of this invention is to provide a method of producing dimethyl dimethoxymalonate.

Other objects of this invention will be apparent to those skilled in the art from the description herein.

A process has been discovered for the production of pyrogallol by reacting glutaric ester with dialkoxymalonic ester in about a 1:1-2 mole ratio at a temperature of about 60°-100° C in the presence of a condensation-promoting base to form a carbocyclic condensation product, converting the resulting condensation product to 4,5,6-trihydroxyisophthalic acid by treating with a suitable acid which is then converted to pyrogallol by heating in the presence of methanol.

DETAILED DESCRIPTION

The reactions which form the process of this invention are discussed in detail below and can be illustrated by the following typical equations:

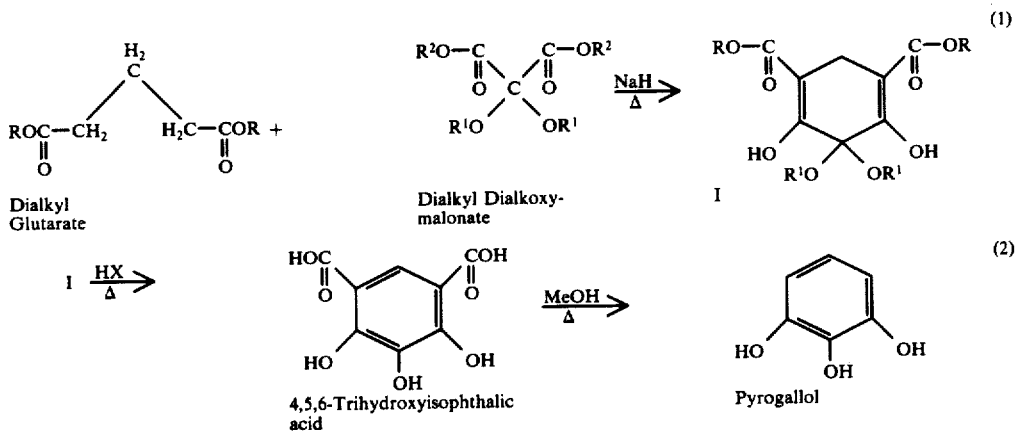

R, $R^1$ and $R^2$ in the above equations can be any lower alkyl radical, e.g. of from 1 to about 6 carbon atoms or more, preferably methyl or ethyl.

In the synthesis of pyrogallol by the process of the present invention, a dialkyl glutarate, e.g. dimethyl glutarate, is reacted with a dialkyl dialkoxy malonate ester, e.g. dimethyl dimethoxy malonate, in about a 1:1 mole ratio in the presence of a condensation-promoting base to provide a dialkyl-4,6-dihydroxy-5,5-dialkoxy-3,6-cyclohexadiene-1,3-dicarboxylate. The reaction can advantageously be carried out in the presence of an inert solvent, e.g. benzene, toluene or xylene at temperatures from ambient to reflux, e.g. from about 25° to about 150° C. Preferably the reaction is carried out under a nitrogen atmosphere. Generally the condensation base is dispersed in the malonate ester and solvent and the glutarate ester is added gradually. After addition is complete, e.g. after 5-8 hours, the mixture is preferably, but not necessarily, heated at reflux, e.g. 60°-150° C. If benzene is used as the solvent, the temperature will be in the range of 60°-100° at the usual atmospheric pressure.

The reaction time will vary widely with the temperature, e.g. from about 10 to about 96 hours. At ambient temperatures, several days, e.g. 48-96 hours or more may be required. At 60°-100°, from about 30 hours to about 20 hours respectively, may be required and at 100°-150°, from about 10 to about 20 hours is typical.

In the next step of the synthesis, the dialkyl-4,6-dihydroxy-5,5-dialkoxy-3,6-cyclohexadiene-1,3-dicarboxylate is treated with a mineral acid to produce 4,5,6-trihydroxyisophthalic acid. The reaction can be carried out at room temperature, e.g. 30°, but preferably elevated temperatures up to 150° C are preferred. Generally, therefore, the reaction can be carried out at from about 30° to about 150° C over a period of from about 20 to 30 hours or more at the lower temperature to about 20 to 30 min. at the higher temperatures. Preferably a temperature of about 120°-130° for a period of 20-40 min. is employed. The reaction is also preferably, but not necessarily, carried out under a nitrogen atmosphere.

It is to be understood that the foregoing reaction temperatures and reaction times are not critical but are merely typical of those convenient to use and it is not intended that the invention be limited thereby. As is generally recognized in the art, the higher the temperature, the shorter the reaction time.

The final step of the synthesis is to convert the 4,5,6-trihydroxyisophthalic acid to pyrogallol. This step can be effected by heating the acid to about 200° C or more, preferably from about 190° to about 210° and preferably, but not necessarily, in the presence of a solvent, such as a lower aliphatic alcohol of from 1 to 4 carbon atoms. Methanol is a preferred solvent. From 4 to about 8 hours is generally required, usually about 6. The reaction is preferably carried out under a nitrogen atmosphere.

The condensation-promoting base used in reaction (1) can be sodium hydride, as shown, or any others known in the art, e.g. sodium alkoxides.

The acid represented by HX in reaction (2) can be any strong acid known in the art which will not react with the other reactants. Suitable acids include but are not limited to mineral acids, e.g. sulfuric, hydrochloric, hydrobromic and organic acids such as trichloroacetic, arylsulfonic acid, e.g. p-toluene sulfonic acid, and the like. Generally an inexpensive acid such as dilute sulfuric (e.g. about 50% or less) or hydrochloric will be preferred.

The dialkyl glutaric ester employed in the practice of this invention can be any alkyl or aryl glutaric acid ester. Generally however the lower alkyl esters, e.g. an alkyl group having from 1 to about 6 carbon atoms, will be preferred for reasons of economy. Dimethyl glutarate is a preferred ester. It is known in the art and can be prepared by any known method; it can also be obtained commercially.

The dialkyl dialkoxymalonate employed in the practice of this invention can be any alkyl or dialkoxymalonate known in the art. Generally the alkyl and alkoxy groups will be lower alkyl, i.e: of from 1 to about 6 carbon atoms, preferably methyl. The methyl compound can be prepared by any method known in the art, e.g. the method of Y. Otsuji et al., Tetrahedron, Vol. 26, 4293 (1970).

However it is an embodiment of the present invention to provide a method for the preparation of dialkyl dialkoxymalonate by the steps of mixing trialkyl orthoformate with dihydroxymalonic acid in a mole ratio of about 5–15 to 1 respectively, heating to within about 90°–110°, preferably at reflux temperature of about 100°–105° C, separating excess trialkyl orthoformate and low-boiling by-products of the reaction by slowly distilling them at ambient pressure from the reaction mixture, and recovering dialkyl dialkoxymalonate by distillation at reduced pressure.

The invention will be better understood by reference to the following example. It is understood, however, that the example is intended only for illustration and it is not intended that the invention be limited thereby.

EXAMPLE

Dimethyl dimethoxymalonate was prepared by mixing trimethyl orthoformate, 300 ml (285 g or 2.8 mol) with 35 g of dihydroxymalonic acid (0.257 mol) in a reaction vessel equipped with a heat source, an agitator and a distillation column. The mixture was heated to the boiling point, 100°–105°, and excess trimethyl orthoformate and by-products were separated by slowly distilling over a period of 13 hours until 250 ml had been collected. The distillation was continued under reduced pressure and the product was collected at 110° C at a pressure of 7 mm.

A 38.4 g (0.2 mol) portion of the dimethyl dimethoxymalonate prepared as above was dissolved in 350 ml anhydrous benzene in a reaction vessel under a nitrogen atmosphere to prevent any tendency to oxidation, if any, using magnetic stirring. A reflux condenser fitted with a water separator was connected to the vessel and a 100 ml portion of the benzene was distilled to remove any residual moisture and to dry the apparatus. The mixture was cooled and sodium hydride (16.9 g of a 57% dispersion in mineral oil) and 1 ml of anhydrous methanol were added. The mixture was heated to reflux and dimethyl glutarate, 16 g (0.1 mol), dissolved in 150 ml of anhydrous benzene was gradually added over a period of 6.5 hr. The mixture was heated an additional 16 hr under reflux and was then cooled in an ice bath. Water, 250 ml, was slowly and cautiously added over an extended period of time and stirring was continued for 30 minutes at room temperature. The mixture was then filtered and the aqueous layer was separated. The aqueous layer was washed with 100 ml of ethyl ether and the pH of the aqueous layer was adjusted to 4 with acetic acid (60 ml) to precipitate the crude product. The crystals were separated by filtration, washed with water and air dried to yield dimethyl 4,6-dihydroxy-5,5-dimethoxy-3,6-cyclohexadiene-1,3-dicarboxylate, m.p. 143°–144°. The infra-red absorption spectrum and the proton magnetic resonance spectrum were consistent with the proposed structure, as were the carbon-hydrogen ratios.

The compound prepared according to the foregoing paragraph, 1 g, was treated with 20 ml of 48% hydrogen bromide at reflux temperature (126° C) for a period of 30 min. under a nitrogen atmosphere to prevent any possible oxidation. The reaction mixture was then cooled in an ice bath and the precipitate was filtered, washed with water and air dried to yield crude 4,5,6-trihydroxyisophthalic acid, mp >300. The infra-red absorption spectrum, proton magnetic resonance spectrum and ultra-violet absorption spectrum were superimposable with the spectrum obtained on a sample prepared by the method of K. Feist and W. Awe. *Chem. Ber.*, 59, 175 (1926).

A 2 g portion of 4,5,6-trihydroxyisophthalic acid was dissolved in 200 ml of methanol and heated at 200° C for 6 hours under a nitrogen atmosphere. The solution was filtered and evaporated to yield crude pyrogallol. Sublimation in vacuo gave white crystals m.p. 126°–128° undepressed by adding thereto crystals from an authentic sample. Also, the infra-red and proton magnetic resonance spectra were identical.

I claim:

1. A process for the production of pyrogallol comprising the steps of
    a. reacting dialkyl glutarate with dialkyl dialkoxymalonate, said alkyl and alkoxy groups having from 1–6 carbon atoms in about a 1 to 1–2 mole ratio at a temperature of about 25°–150° in the presence of sodium hydride or a sodium alkoxide thereby producing dialkyl-4,6-dihydroxy-5,5-dimethoxy-3,6-cyclohexadiene-1,3-dicarboxylate, and separating same,
    b. heating said dialkyl 4,6-dihydroxy-5,5-dimethoxy-3,6-cyclohexadiene-1,3-dicarboxylate in the presence of a strong acid selected from the group consisting of sulfuric, hydrochloric, hydrobromic, trichloroacetic and p-toluene sulfonic acid at a temperature of from about 30° to about 150° C to produce 4,5,6-trihydroxyisophthalic acid, and separating same, c. heating said trihydroxyisophthalic acid at a temperature of about 190°-210° C to produce pyrogallol.

2. The process of claim 1 wherein said alkyl and alkoxy are hydrocarbon radicals of from 1 to 6 carbon atoms.

3. The process of claim 2 wherein said alkyl and alkoxy are methyl groups.

4. The process of claim 1 wherein said dialkyl glutarate is dimethyl glutarate.

5. The process of claim 1 wherein said dialkyl dialkoxymalonate is dimethyl dimethoxymalonate.

* * * * *